US010639420B2

(12) United States Patent
Le Maitre et al.

(10) Patent No.: US 10,639,420 B2
(45) Date of Patent: May 5, 2020

(54) SHIELDING DEVICE USEFUL FOR MANIPULATING A RADIOACTIVE SOLUTION

(71) Applicant: SIMPLIVIA HEALTHCARE LTD., Kiryat Shmona (IL)

(72) Inventors: Julien Le Maitre, Malabry (FR); Pierre-Marie Lemer, Malabry (FR)

(73) Assignee: SIMPLIVIA HEALTHCARE LTD., Kiryat Shmona (IL)

( * ) Notice: Subject to any disclaimer, the term of this patent is extended or adjusted under 35 U.S.C. 154(b) by 475 days.

(21) Appl. No.: 15/611,897

(22) Filed: Jun. 2, 2017

(65) Prior Publication Data

US 2017/0348485 A1    Dec. 7, 2017

(30) Foreign Application Priority Data

Jun. 3, 2016  (EP) .................................... 16172870

(51) Int. Cl.
*A61M 5/178* (2006.01)
*A61J 1/20* (2006.01)
(Continued)

(52) U.S. Cl.
CPC .......... *A61M 5/1785* (2013.01); *A61J 1/1406* (2013.01); *A61J 1/16* (2013.01);
(Continued)

(58) Field of Classification Search
CPC ...... A61M 5/1785; A61M 5/1782; A61J 1/16; A61J 1/2096; A61J 1/201; A61J 1/1406
See application file for complete search history.

(56) References Cited

U.S. PATENT DOCUMENTS

| 6,162,198 A | 12/2000 | Coffey et al. |
| 2010/0006156 A1 | 1/2010 | Schilp et al. |
| 2013/0331691 A1 | 12/2013 | Uber, III et al. |

FOREIGN PATENT DOCUMENTS

| WO | 2005/041846 A2 | 5/2005 |
| WO | 2007016171 A2 | 2/2007 |

(Continued)

*Primary Examiner* — Leslie R Deak
(74) *Attorney, Agent, or Firm* — David S. Safran; Roberts Calderon Safran & Cole, P.C.

(57) ABSTRACT

The present disclosure relates to a device (1) for sampling and/or injection of a radioactive solution (S) in a vial (2), wherein the vial (2) comprises an opening closed by a puncturable closure member (3).

The device (1) comprises a container (7) adapted to receive said vial (2) and a vial adaptor (4), said vial adaptor (4) having a longitudinal axis (L1), provided at a first end (41) with a hollow spike (42) adapted to pierce said puncturable closure member (3) when the vial adaptor (4) is mounted on the vial (2), and at a second end (43) with connection means (5) adapted for its removable connection to a syringe (6), the container (7) comprising:

- a container body (71) adapted to receive said vial (2), the container body (71) having an opening (711), and
- a vial adaptor support structure (72) configured for being mounted onto the opening (711) of the container body (71), and comprising retention means configured for enabling releasable retention of said vial adaptor (4) within said vial adaptor support structure (72), and
- wherein the vial adaptor support structure (72) and the container body (71) are made at least partially of a radioprotective material for providing protection against ionizing radiation.

9 Claims, 6 Drawing Sheets

(51) Int. Cl.
    *A61J 1/16*        (2006.01)
    *A61J 1/14*        (2006.01)

(52) U.S. Cl.
    CPC ............ *A61J 1/201* (2015.05); *A61J 1/2048* (2015.05); *A61J 1/2096* (2013.01); *A61M 5/1782* (2013.01); *A61J 1/2075* (2015.05); *A61J 1/2082* (2015.05)

(56) References Cited

FOREIGN PATENT DOCUMENTS

| | | | |
|---|---|---|---|
| WO | 2007140238 | A2 | 12/2007 |
| WO | 2008083313 | A2 | 7/2008 |
| WO | 2009007350 | A1 | 12/2009 |
| WO | 2013184640 | A2 | 12/2013 |

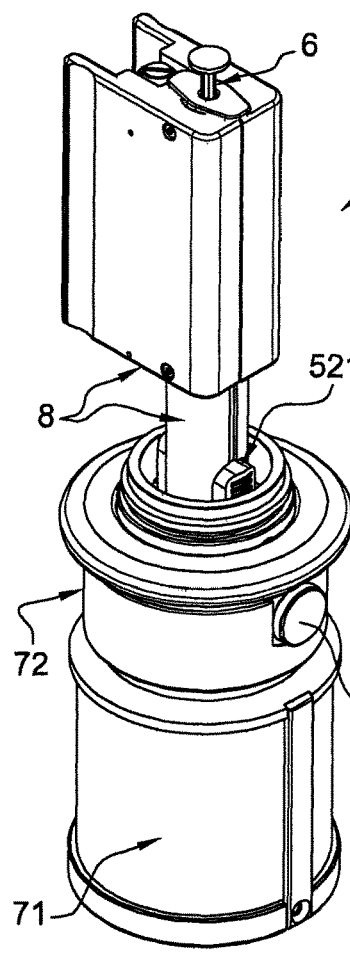
Fig. 1
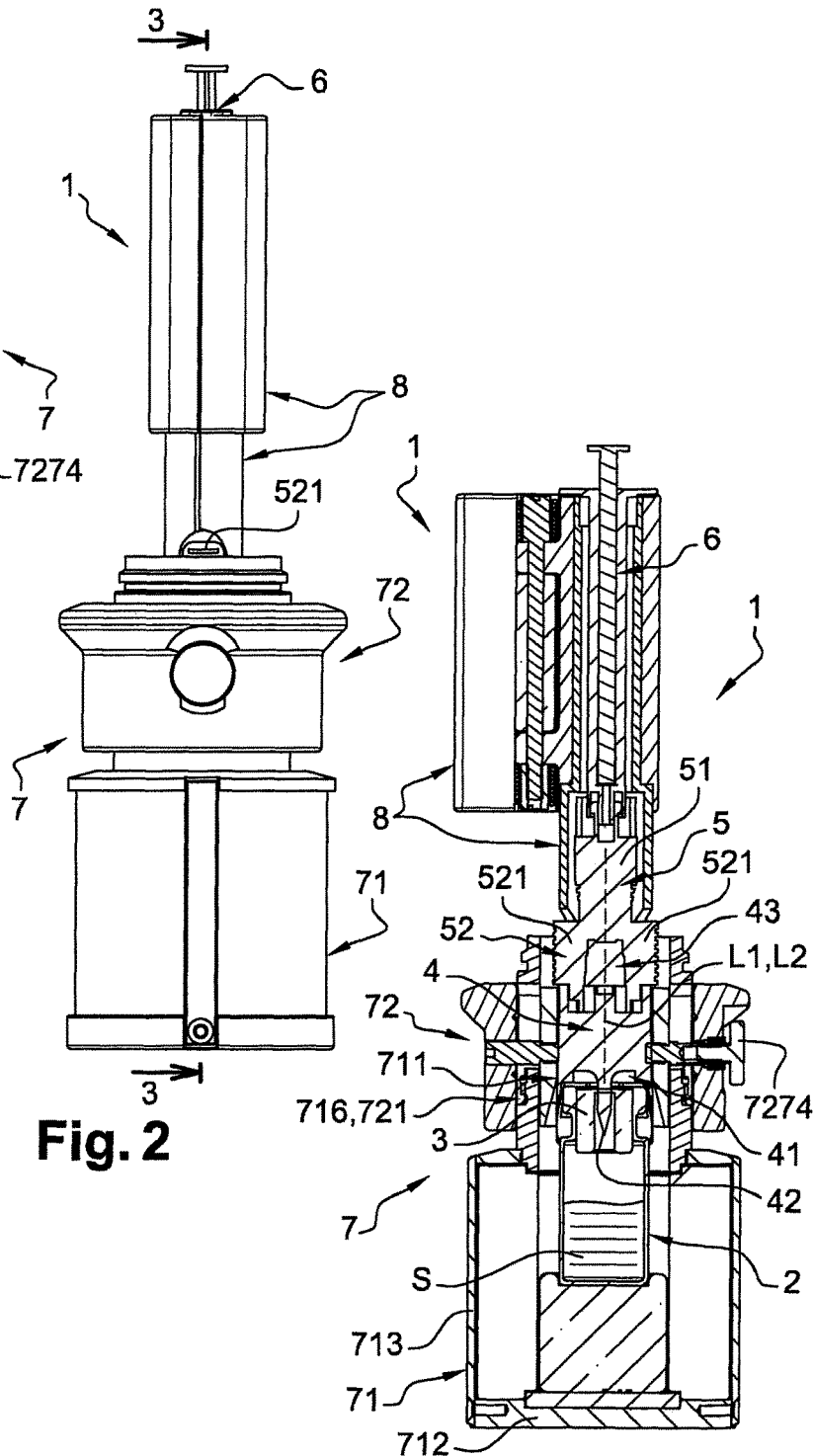
Fig. 2
Fig. 3

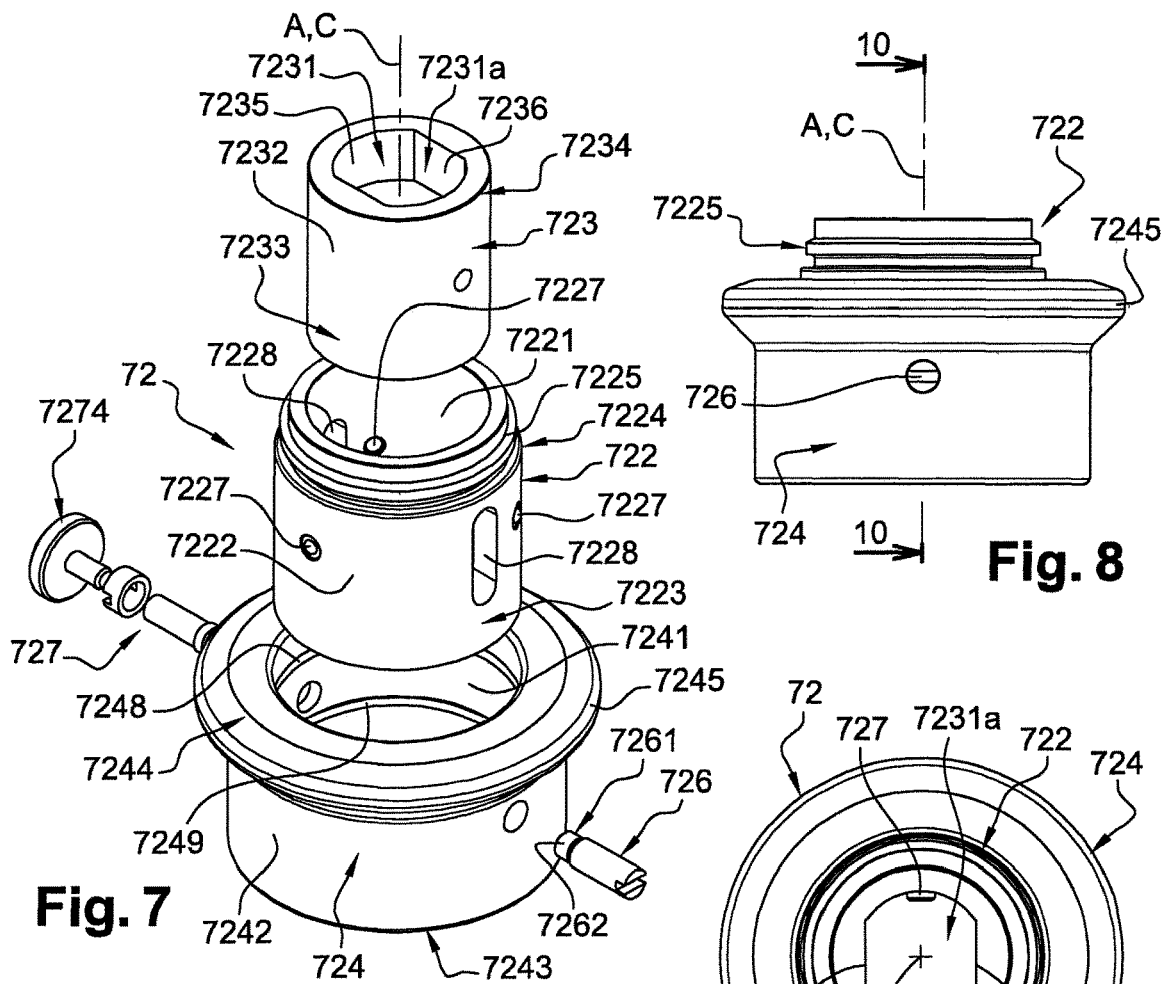
Fig. 7
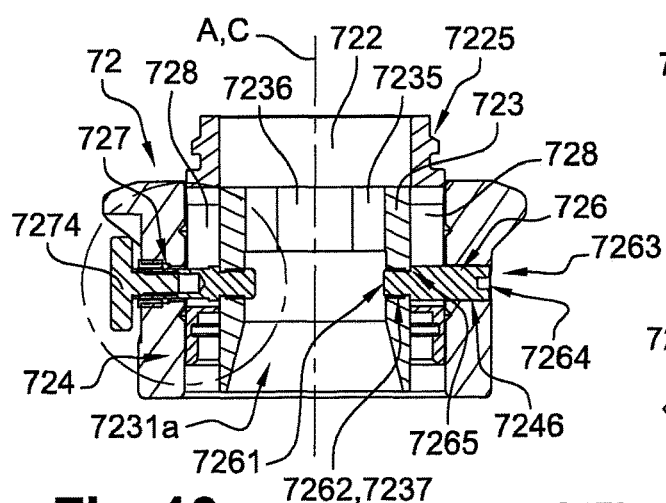
Fig. 10
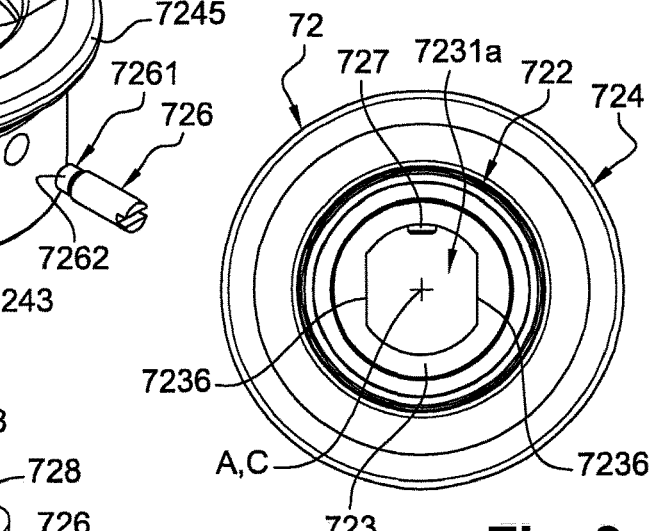
Fig. 8
Fig. 9
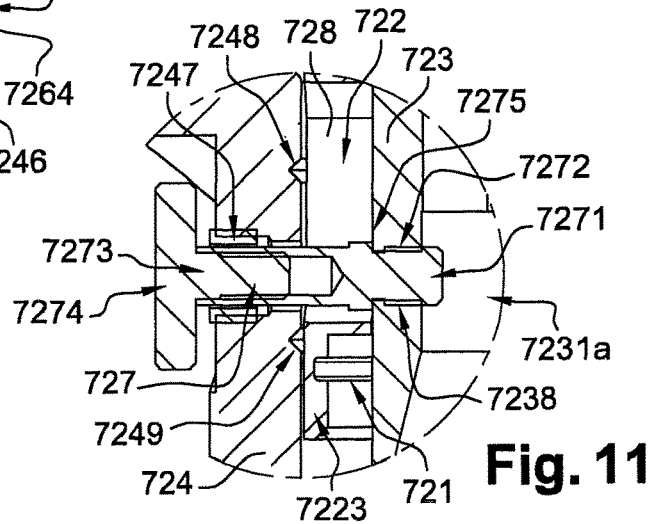
Fig. 11

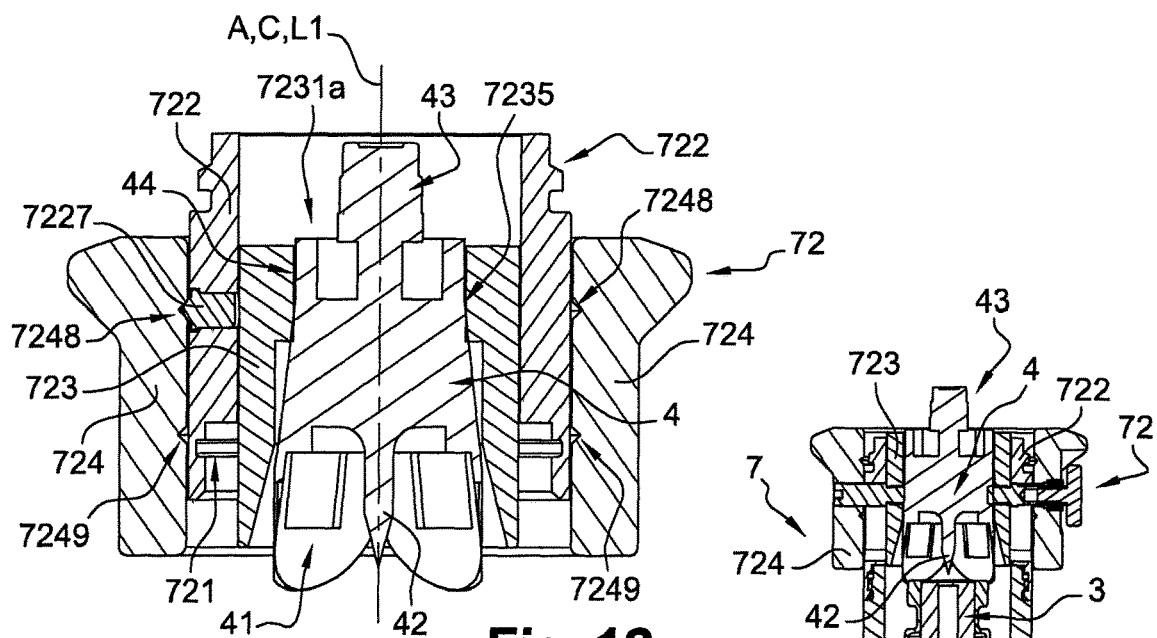
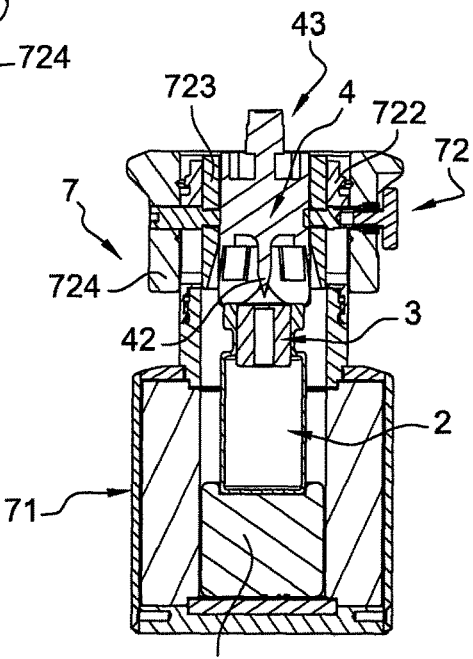
Fig. 12
Fig. 13
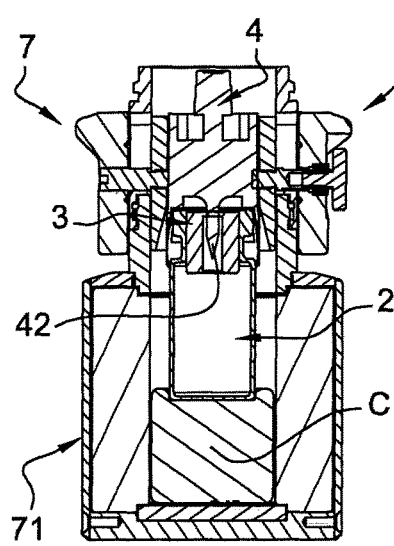
Fig. 14
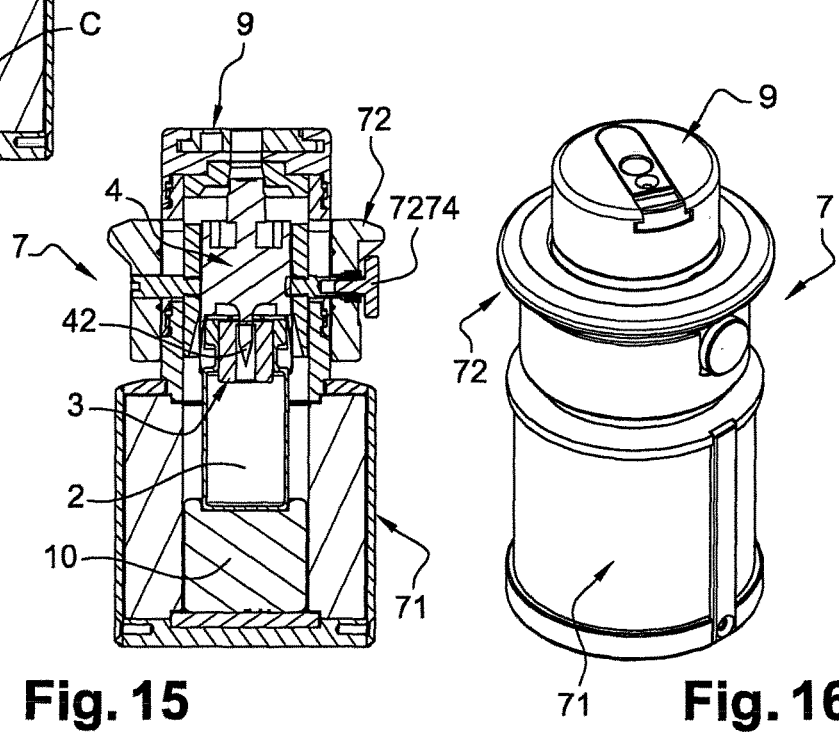
Fig. 15
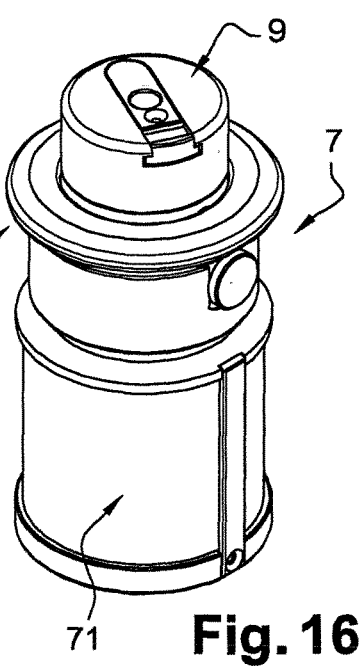
Fig. 16

SHIELDING DEVICE USEFUL FOR MANIPULATING A RADIOACTIVE SOLUTION

TECHNICAL FIELD OF THE PRESENT DISCLOSURE

The present disclosure relates generally to the field of the preparation of injectable solutions using a syringe. More particularly, the present disclosure relates to a shielding device usable for sampling and/or injection of a radioactive solution contained in a vial closed by a puncturable closure member.

BACKGROUND ART

Document WO-2005/041846, enclosed herein by reference, discloses an equipment which is suitable in particular for sampling a solution in a vial whose opening is sealed by a puncturable closure member (generally referred to as a septum vial), or to inject a solution into said vial, this by means of a syringe.

This equipment comprises two parts which can be assembled together in a removable manner.

As shown for example in FIG. 1A of WO-2005/041846 with reference 30, one of them, called "vial adaptor", is adapted to be mounted on said vial. As shown for example in FIG. 1C of WO-2005/041846 with reference 50, the other, called "syringe adaptor" is adapted to be mounted on the tip of the body of a syringe.

The vial adaptor is in the form of a longitudinal piece provided at a first end with a hollow spike adapted to pierce the puncturable closure member of the vial (septum), and at a second end with means adapted for its removable connection to a syringe through the syringe adaptor.

The vial adaptor and syringe adaptor are assembled or disassembled with each other depending on the desired operations of sampling or injection of the solution used.

SUMMARY OF THE DISCLOSURE

However, as such, the equipment disclosed in WO-2005/041846 is not suitable for sampling and injection of radioactive solutions, for example used in the medical field for the diagnosis or treatment of various diseases.

Indeed, these radioactive solutions are generally prepared on site, from a radioisotope generator that provides a stock solution (packaged in a vial whose opening has a puncturable closure member) from which different elution volumes are taken to be injected to patients after quantification of activity.

For example, the stock solution is a technetium 99 solution obtained from molybdenum 99. From the preparation of the radioactive stock solution to the injection operation of the elution volumes, operators must be efficiently protected against ionizing radiation emitted by the radioactive solution manipulated.

Therefore, the present disclosure provides a shielding device (or assembly) useful for sampling and/or injection of a radioactive solution, the shielding device being adapted to cooperate with a vial adaptor and syringe adaptor equipment, as described above, the device being provided with means adapted to ensure effective protection of the operators against ionizing radiation emitted by radioactive solutions implemented.

Furthermore, it should be noted that the puncturing operations of the puncturable closure member of the vial by the hollow spike of the vial adaptor should be performed with care since incorrect puncture may lead to unwanted leakages.

In particular, to avoid or limit the damages of the puncturable closure member, it is preferable to carry out the puncture according to a translation perpendicular to the plane of the puncturable closure member.

Therefore, another object of the present disclosure may be to provide such a device for sampling and/or injection which allows obtaining an effective piercing of the puncturable closure member of the vial containing the radioactive solution by the hollow spike of the vial adaptor.

Still another object of the present disclosure may be to provide an efficient radioprotective system of the sampling and injection syringe, very easy to set up and remove.

For this the device according to the present disclosure, useful for sampling and/or injection of a radioactive solution in a vial, wherein the vial has an opening closed by a puncturable closure member, comprises:

a container adapted to receive said vial and a vial adaptor, said vial adaptor having a longitudinal axis, provided at a first end with a hollow spike adapted to pierce said puncturable closure member when the vial adaptor is mounted on the vial, and at a second end with connection means adapted for its removable connection to a syringe, the container comprising:
a container body adapted to receive said vial, the container body having an opening, and
a vial adaptor support structure configured for being mounted onto the opening of the container body, and comprising retention means configured for enabling releasable retention of said vial adaptor within said vial adaptor support structure, and wherein the vial adaptor support structure and the container body are made at least partially of a radioprotective material for providing protection against ionizing radiation.

According to an embodiment of the present disclosure said vial adaptor support structure comprises transfer means for imparting to said vial adaptor a degree of freedom in longitudinal translation along its longitudinal axis, to optimize the piercing operation of the puncturable closure member of the vial. It is noted that a translation is herein understood according to its common meaning i.e. a movement that changes the position of an object, moving every point the same distance in the same direction, without rotation, reflection or change in size (see for example Wikipedia "Translation in Physics"). In other words, the transfer means are configured to impart to the vial adaptor a pure translational motion along its longitudinal axis i.e. one (a single) degree of freedom in longitudinal translation along its longitudinal axis. This enables to carry out the puncture of the closure member according to a translation movement perpendicular to the plane of the said closure member, when the vial is received in the container body and the vial adaptor is mounted on the container body. The translational puncturing advantageously limits damages done on the vial septum.

In some embodiments, the vial adaptor support structure further comprises indexing means into at least a upper position and a lower position of the vial adaptor with respect to the vial adaptor support structure. In some embodiments, the indexing means may provide indexing into a set of vertical positions of the vial adaptor with respect to the vial adaptor support structure. This allows easy positioning of the vial adaptor.

In some embodiments, the vial adaptor support structure is generally tubular with a longitudinal axis and comprises:
- a tubular sleeve having a first end provided with attachment means configured for enabling mounting of the vial adaptor support structure onto the opening of the container body,
- a support ring, received in said tubular sleeve, coaxial with the tubular sleeve, and defining an internal space for the reception of said vial adaptor, wherein the transfer means are further configured for imparting to said support ring a degree of freedom in longitudinal translation along said longitudinal axis with respect to said tubular sleeve, and the retention means are further configured for enabling connection of said vial adaptor with said support ring. In other words, the retention means enable attachment/holding of the vial adaptor within the support ring. In other words, the retention means configured for being able to selectively secure and free the vial adaptor into/from the support ring.

In some embodiments, the vial adaptor support structure advantageously comprises a jacket for operating said support ring according to said degree of freedom in translation, the jacket at least partially surrounding said tubular sleeve and including fastening means configured to fasten said jacket with said support ring.

Said fastening means are preferably in the form of at least two assembly lugs connecting said jacket and said support ring, and which pass through oblong holes in said tubular sleeve.

According to yet another feature, said retention means comprise a radial bearing pin secured with said jacket and/or said support ring, wherein said bearing pin has an outer end accessible on an outer periphery of said jacket, provided with an operating member, and an inner end forming a bearing head, and wherein said bearing pin is movable radially between:
an active position in which said bearing head extends into said internal space of said support ring and is adapted to abut against said vial adaptor in order to maintain said vial adaptor within said support ring and/or said jacket, and
an inactive position in which said bearing head does not abut against said vial adaptor.

The bearing pin is advantageously also one of said assembly lugs.

Still according to another feature, the device further includes indexing means to at least one position of an assembly comprising the vial adaptor, the support ring and the jacket, relative to said tubular sleeve.

Preferably, said indexing means comprise at least one retractable ball lock mounted on one of the assembly or the tubular sleeve, cooperating with a recess provided on the other of the assembly or the tubular sleeve.

According to a preferred embodiment, said tubular sleeve is made of radioprotective material providing protection against ionizing radiation.

Preferably, a second end of said tubular sleeve opposite to the first end includes connection means for removably fixing a cover made of radioprotective material providing protection against ionizing radiation.

According to yet another advantageous feature, said support ring comprises first positioning means configured for blocking said vial adaptor in a direction along its longitudinal axis, and second positioning means adapted to prevent rotation of said vial adaptor about said longitudinal axis.

Still according to another feature, the device further comprises a syringe comprising a syringe body, a piston and a syringe adaptor configured for connection to said vial adaptor, and a protection device shaped as a shield made of radioprotective material providing protection against ionizing radiation, wherein said protection device covers at least partially said syringe body and said syringe adaptor.

The present disclosure also provides a protection device for a syringe having a syringe body extending along a longitudinal axis and comprising, at a first end, an end tip including an orifice for the passage of liquid, and, at a second end, an opening for the passage of a piston provided with a maneuver head, wherein the protection device is adapted to at least partially cover said syringe body and is made at least in part of a radioprotective material providing protection against ionizing radiation, and wherein the protection device is in the form of a clamp comprising two half-jaws joined together by a hinge, which clamp includes operating means adapted so that said half-jaws are moveable between:
- a closed operative position, in which said half-jaws are assembled as a cylinder to at least partially cover said syringe body, and
- an open inactive position, adapted for the introduction and extraction of said syringe body, said hinge being provided with biasing means tending to maintain said closed operative position.

In this protection device for syringe, preferably, each half-jaw comprises a half-shell made of a radioprotective material providing protection against ionizing radiation, wherein said half-shell have a semi-cylindrical cross section, which is assembled with a base of plastics material, wherein a longitudinal edge of each of said bases forms part of said hinge in association with said biasing means, said bases of the two half-jaws being configured so that projections project on the other side of said hinge, said projections constituting actuating arms for the operations of opening and closing of the clamp.

Each half-shell, made of a radioprotective material providing protection against ionizing radiation, is advantageously assembled with its base by means of screws assembly.

In a particular embodiment, said end tip of said syringe comprises a syringe adaptor adapted for connection to another equipment such as a vial adaptor, and said half-shells made of a radioprotective material providing protection against ionizing radiation, each comprises a protrusion adapted to cover at least in part said syringe adaptor.

The present disclosure also provides a method for preparing a syringe containing a radioactive solution using a device as described above.

In some embodiments, the method comprises:
providing a vial containing said radioactive solution in a container body having an opening, the vial being closed by a puncturable closure member and the container body being made at least partially of a radioprotective material,
inserting a vial adaptor provided at a first end with a hollow spike adapted to pierce said puncturable closure member when the vial adaptor is mounted on the vial, and at a second end with connection means adapted for its removable connection to a syringe adaptor in a vial adaptor support structure by using releasable retention means of said vial adaptor support structure, the vial adaptor support structure being made at least partially of a radioprotective material,
mounting the vial adaptor support structure onto the opening of the container body.

In some embodiments, mounting the vial adaptor support structure onto the opening of the container body positions the vial adaptor just above the vial, coaxially thereto, and in particular to its opening, and with the hollow spike positioned facing the puncturable closure member, at a slight distance from this puncturable closure member, and the method further comprises: positioning the vial adaptor on the upper portion of the vial, by translating the vial adaptor, with respect to a tubular sleeve of the vial adaptor support structure, to ensure the piercing of the puncturable closure member, by the hollow spike of the vial adaptor, and; connecting the syringe to a syringe adaptor and then the syringe and syringe adaptor to the vial adaptor for sampling said radioactive solution.

The present disclosure also provides a method for preparing a syringe containing a radioactive solution by using a device as previously described, the method comprising: introducing a vial containing said radioactive solution and whose opening is closed by a puncturable closure member, in the container body; connecting the vial adaptor with said support ring of the vial adaptor support structure by using the retention means; mounting the vial adaptor support structure onto the opening of the container body, the vial adaptor being positioned just above the vial, coaxially thereto, and in particular to its opening, and with the hollow spike positioned facing the puncturable closure member at a slight distance from this puncturable closure member; positioning the vial adaptor on the upper portion of the vial, by lowering the assembly comprising the support ring, the jacket and the vial adaptor, with respect to the tubular sleeve, to ensure the piercing of the puncturable closure member by the hollow spike of the vial adaptor, and; connecting the syringe to the vial adaptor for sampling said radioactive solution.

DETAILED DESCRIPTION OF EXAMPLE(S)

The following description related to the appended drawings given by way of non-limiting example, explains in what the present disclosure is and how it can be achieved.

In the accompanying drawings:

FIG. 1 is a general perspective view of a device for sampling and/or injection of a radioactive solution in a vial according to the present disclosure, with the vial adaptor and the syringe adaptor assembled together, the vial adaptor being in position on the vial containing the radioactive solution, this assembly being placed in a container made of radioprotective material, and the syringe adaptor being assembled with the sampling/injection syringe, also associated with its own radioprotective means;

FIG. 2 is a side view of the device illustrated in FIG. 1;

FIG. 3 is a sectional view along section lines 3-3 of FIG. 2;

FIG. 7 is an exploded perspective view of the vial adaptor support structure illustrated in FIG. 6;

FIG. 8 is a side view of the vial adaptor support structure shown in FIG. 6;

FIG. 9 is a top view of the vial adaptor support structure shown in FIGS. 6 and 8;

FIG. 10 is a sectional view of the vial adaptor support structure, taken along section lines 10-10 of FIG. 8;

FIG. 11 is an enlarged view of a detail of FIG. 10;

FIG. 12 is a sectional view of the vial adaptor support structure, in which is positioned the vial adaptor;

FIG. 13 is a sectional view of the container of the sampling/injection device according to the present disclosure, with the assembly comprising the support ring and the jacket of the vial adaptor support structure, supporting said vial adaptor, prior to the piercing of the puncturable closure member;

FIG. 14 is a view similar to FIG. 13, after piercing of the puncturable closure member;

FIG. 15 is a view similar to FIG. 14, showing the vial adaptor support structure associated with a cover made of radioprotective material;

FIG. 16 is a perspective view of the container illustrated in FIG. 15;

Figure 4:
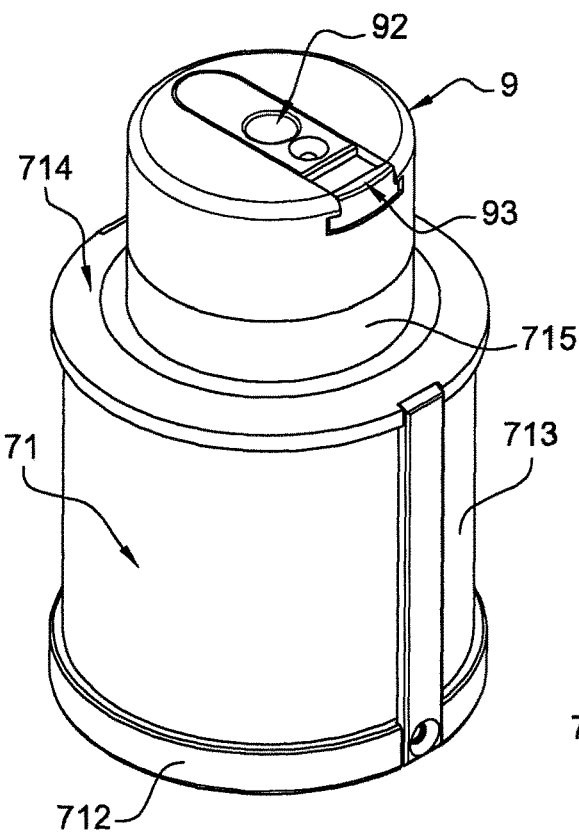
FIG. 4 is a perspective view of the container made of a radioprotective material, without the vial adaptor support structure, and associated with a cover.

In the following detailed description, numerous specific details are set forth in order to provide a thorough understanding of the subject matter. However, it will be understood by those skilled in the art that some examples of the subject matter may be practiced without these specific details. In other instances, well-known methods, procedures and components have not been described in detail so as not to obscure the description.

As used herein, the phrase "for example," "such as", "for instance" and variants thereof describe non-limiting examples of the subject matter.

Reference in the specification to "one example", "some examples", "another example", "other examples, "one instance", "some instances", "another instance", "other instances", "one case", "some cases", "another case", "other cases" or variants thereof means that a particular described feature, structure or characteristic is included in at least one example of the subject matter, but the appearance of the same term does not necessarily refer to the same example.

It should be appreciated that certain features, structures and/or characteristics disclosed herein, which are, for clarity, described in the context of separate examples, may also be provided in combination in a single example. Conversely, various features, structures and/or characteristics disclosed herein, which are, for brevity, described in the context of a single example, may also be provided separately or in any suitable sub-combination.

It is shown in FIGS. 1 to 3 a device 1 of the present disclosure for sampling and/or injecting a radioactive solution S packaged in a vial 2 (here a vial of the type named "Mallinckrodt" (registered trademark)).

The vial 2 is standard. The vial 2 consists of a container made of glass or transparent plastic which ends at the top by a collar or neck delimiting an opening closed by a puncturable closure member 3 (also known as a septum). This closure member 3 may be made of plastics, rubber or the like.

The radioactive solution S may be any solution emitting ionizing radiation, for example technetium 99.

The device 1 for sampling and/or injection therefore may comprise:
- an equipment of the type vial adaptor 4 and syringe adaptor 5 (here joined together), as described in WO-2005/041846, the vial adaptor 4 being in position on the vial 2, and the syringe adaptor 5 being assembled with a syringe 6,
- a container 7 adapted to receive said vial 2 and said vial adaptor 4, which container 7 is made at least in part of a radioprotective material providing protection against ionizing radiation, and
- a shield-shaped protective device 8 made at least in part of a radioprotective material providing protection against ionizing radiation. The shield-shaped protective device 8 may at least partially cover said syringe 6 and said syringe adaptor 5.

The radioprotective materials used are standard in the domain of the devices which provide protection against ionizing radiation. For example these materials consist of tungsten and/or lead glass, whose thicknesses are adapted to the type of radioactive solution used, and depending on the desired protection for operators.

The vial adaptor 4 and the syringe adaptor 5 are here represented in a simplified pictorial illustration and in particular without detailing their internal structure providing fluidic communication therethrough. The vial adaptor 4 and the syringe adaptor 5 can be removably and sealingly connected.

As described in WO-2005/041846, which is herein enclosed by reference in particular with respect to pages 20 to 24 in connection with FIGS. 4 to 7 of that document, and in connection with FIGS. 3 and 12 of the present application:
- the vial adaptor 4 is in the form of an elongated body with a longitudinal axis L1, produced by plastic injection molding, comprising a rear portion 41 (also referred to as vial connection port), of generally cylindrical shape, surrounding a hollow spike 42 for piercing the puncturable closure member 3 of the vial 2, and a front portion 43 (also referred to as syringe adapter element connection port) adapted to be removably and sealingly assembled with a front portion of the syringe adaptor 5. The hollow spike 43 may include a medicament bore (not shown) extending through the hollow spike 43 so as to be in fluid communication with said syringe adapter element connection port 41. The hollow spike 43 may also include a vent bore (not shown) extending through the hollow spike 43 so as to vent the vial adaptor in a manner which prevents release to the atmosphere of possibly harmful contents of said vial. In some embodiments, the vent bore may be in fluid communication with a filter module of the vial adaptor wherein the filter module includes a hydrophobic membrane and/or a carbon cloth filter. The filter module may enable to maintain sterility of the vial contents and protects users from toxic vapors; and
- the syringe adaptor 5 is in the form of an elongated body with a longitudinal axis L2, produced by plastic injection molding, comprising a rear portion 51 adapted to be assembled with the tip of the syringe body 6, and a front portion 52 adapted to be assembled removably and sealingly with said front portion 43 of the vial adaptor 4. This front portion 52 of the syringe adaptor 5 has two lateral extensions 521, diametrically opposed, consisting of elastic hooking structures for detachable connection with the front portion 43 of the vial adaptor 4, the hooking structures 521 being deactivated by manually pressing. In some embodiments, the elongated body of the syringe adaptor defines a lumen which houses a septum housing and a needle. The needle may extend through the syringe adaptor lumen and be configured for establishing fluid communication with the syringe when the syringe is connected to the syringe adaptor. The septum housing may be mounted in the syringe adaptor lumen so as to be slide longitudinally over the needle. The septum housing may include one or more septum made of a resilient material such as rubber or the like. A distal tip of the needle may be enclosed within the septum housing when the syringe adaptor is not connected to a vial adaptor and may protrude out of the septum housing upon connection with the vial adaptor thereby establishing fluid communication between the vial adaptor hollow spike and the syringe.

The container 7, adapted to receive the vial 2 and the vial adaptor 4 is formed at least partly of a radioprotective material providing protection against ionizing radiation (for example tungsten and/or lead glass) and comprises:
- a container body 71 provided with an opening 711 adapted to receive the vial 2, and
- a support structure 72 for said vial adaptor 4, provided with means for its attachment to said opening 711 of the container body 71, and provided with means for the retention or the holding of said vial adaptor 4, detailed below.

Figure 5:
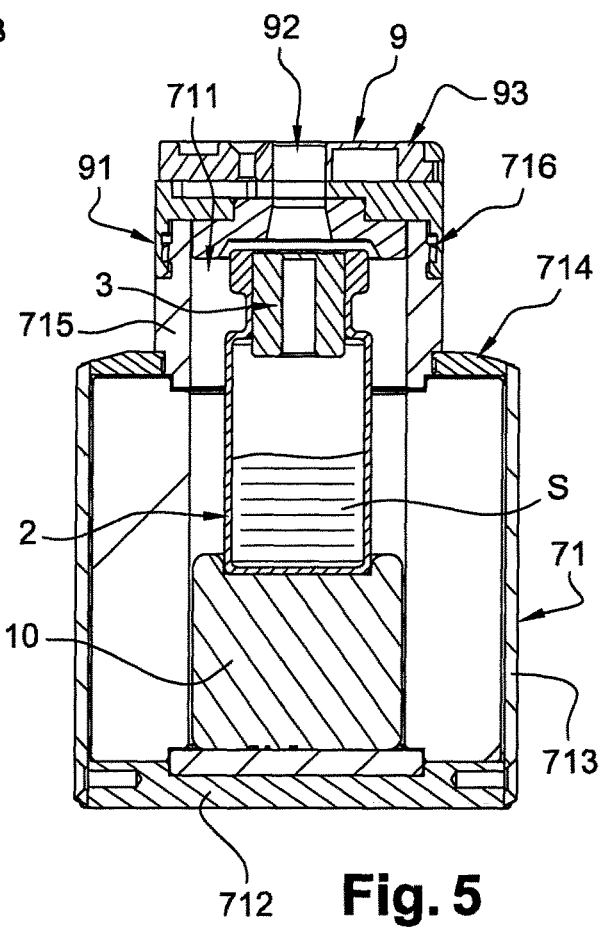
FIG. 5 is a sectional view of the container with cover according to FIG. 4.
Figure 6:
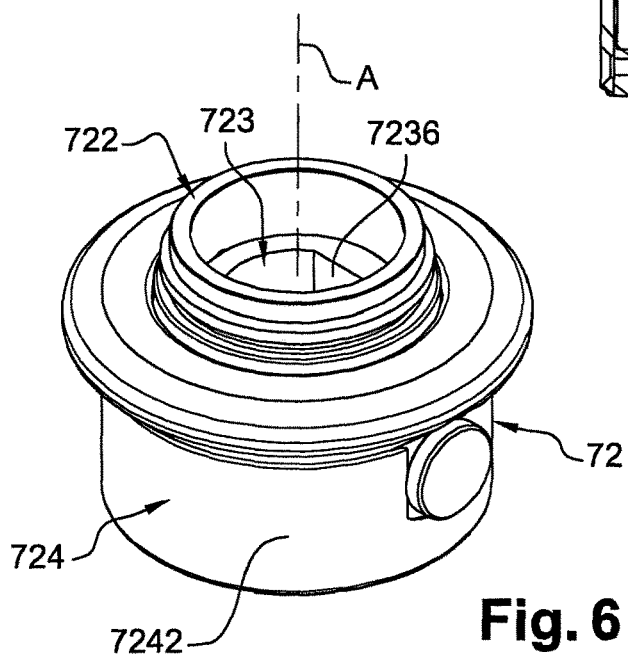
FIG. 6 is a perspective view of the vial adaptor support structure, shown in isolation.
Figure 17:
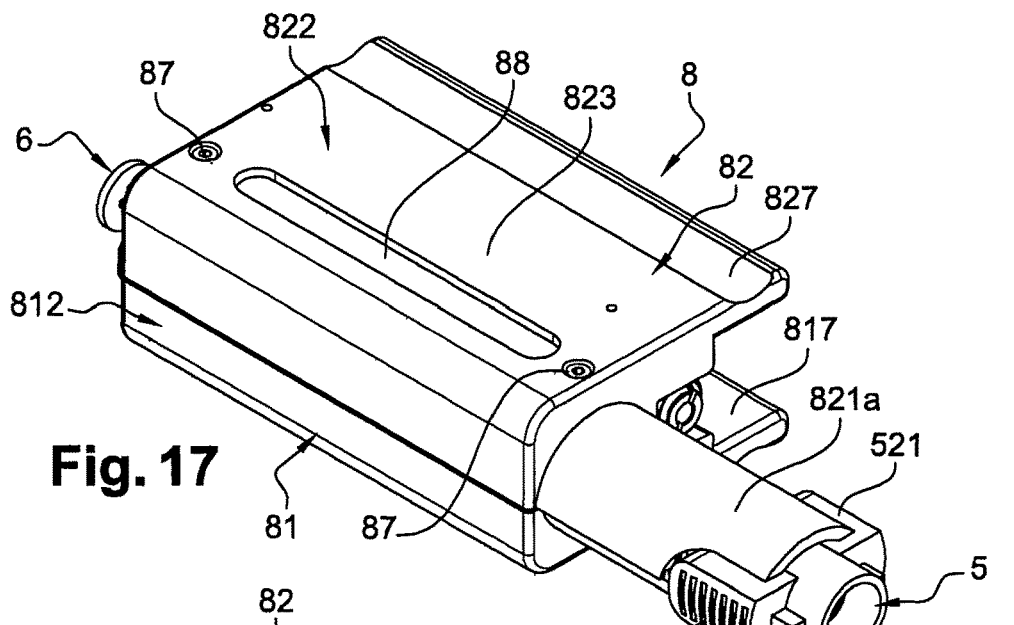
FIG. 17 is a perspective view of the sampling/injection syringe equipped with the syringe adaptor, the assembly being associated with a radioprotective device, here in the active closed position.
Figure 18:
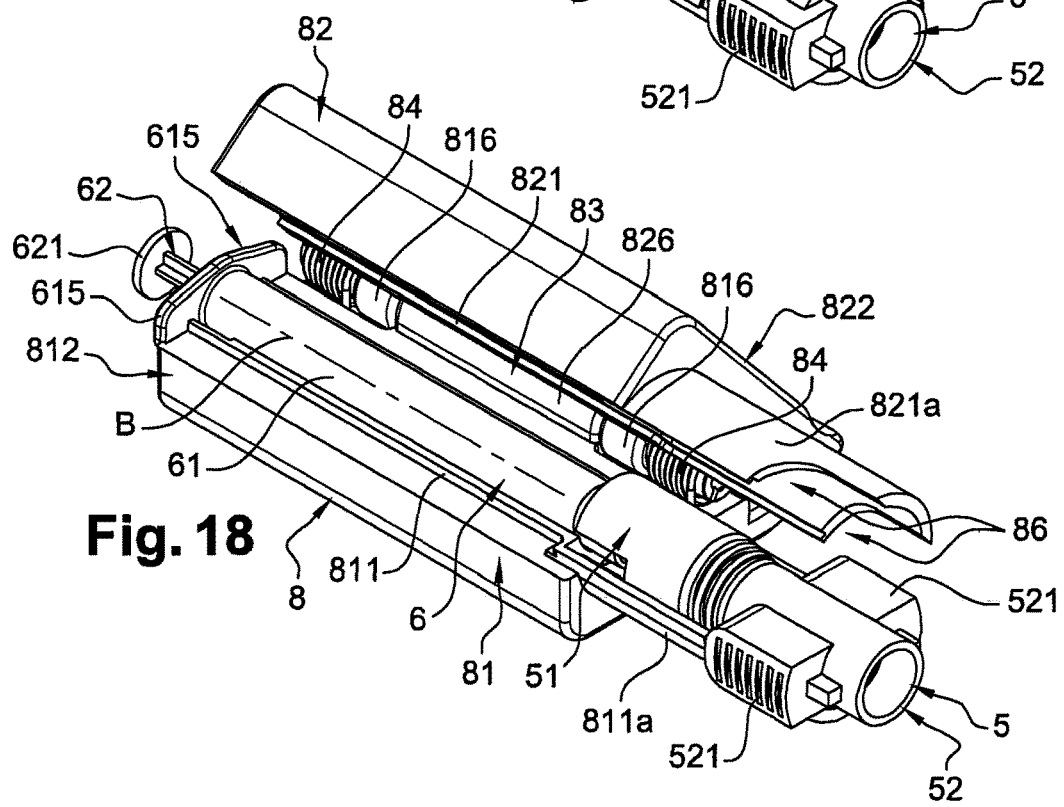
FIG. 18 is a view similar to FIG. 17, the radioprotective device being here in its inactive open position.
Figure 19:
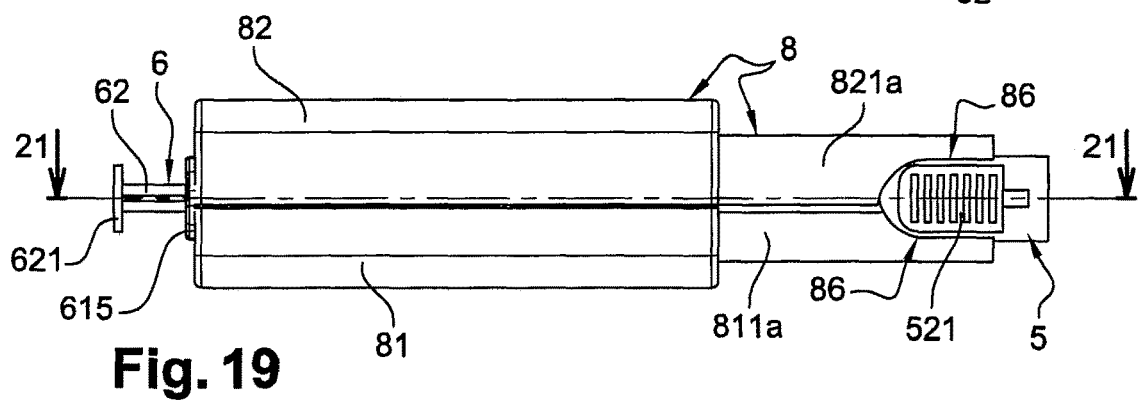
FIG. 19 is a side view of the assembly illustrated in FIG. 17.
Figure 20:
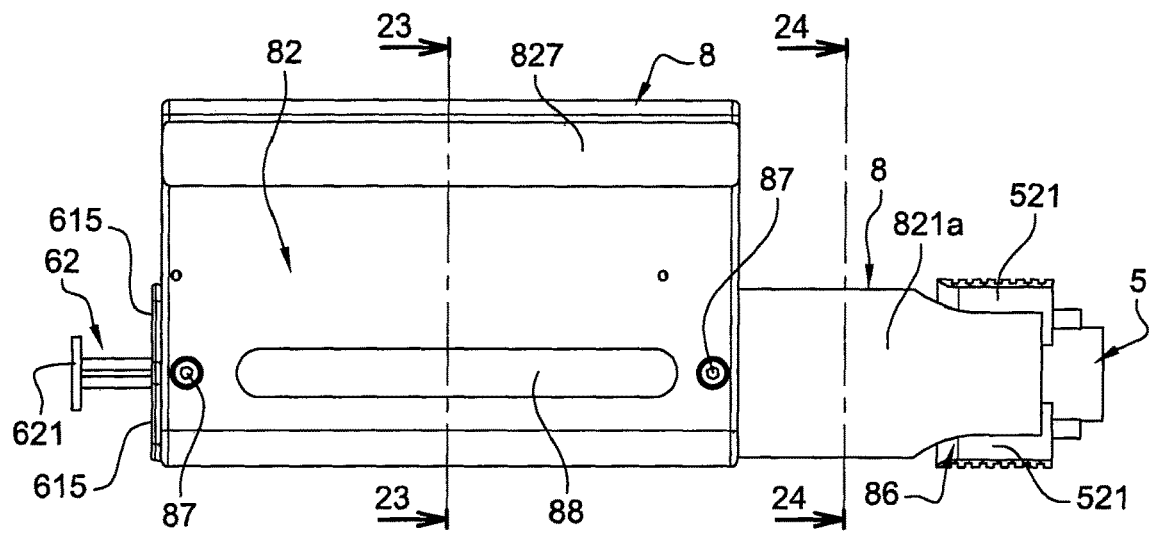
FIG. 20 is a front view of the assembly illustrated in FIGS. 17 and 19.
Figure 21:
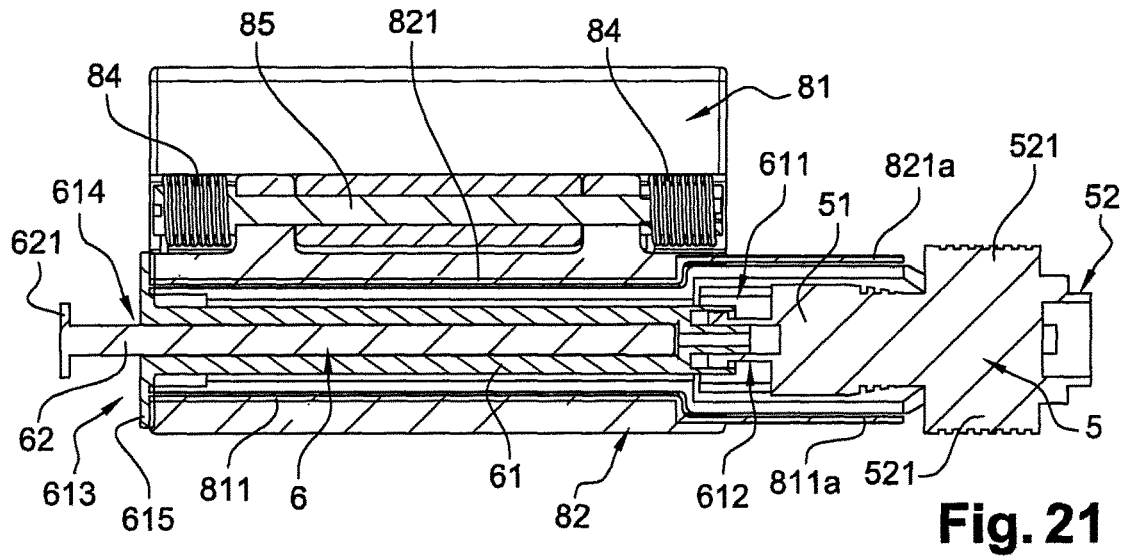
FIG. 21 is a sectional view taken along section lines 21-21 of FIG. 19.
Figure 22:
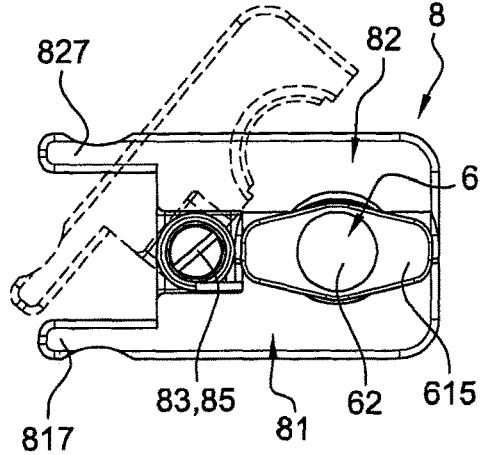
FIG. 22 is an end view of the assembly illustrated in FIGS. 19 and 20.

The container body 71, also shown in FIGS. 4 and 5, comprises a base member 712 which is extended by a cylindrical wall 713. This cylindrical wall 713 comprises, at the top, a circular crown 714 from the central area of which extends a cylindrical collar 715 which defines said opening 711. In some embodiments, the cylindrical wall 713 may include a transparent window to allow visual access to the contents of the container body. In some embodiments, an internal surface of the cylindrical wall 713 may have a bright color such as white or the like.

The outer surface of the cylindrical collar 715 has means for detachable connection with the vial adaptor support structure 72, here in the form of a thread 716. The means for detachable connection between the vial adaptor support structure and the container body may be of any type such as bayonet coupling, quarter turn, snapping, clipping and the like.

This thread 716 is adapted to cooperate with attachment means in the form of a complementary thread 721 of the vial adaptor support structure 72 (FIG. 3), or with a complementary thread 91 of a cover 9 adapted to seal removably the opening 711 of the container body 71 (FIGS. 4 and 5).

The cover 9 is made of a radioprotective material providing protection against ionizing radiation (for example tungsten and/or lead glass).

The vial adaptor support structure 72, shown in isolation in FIGS. 6 to 12, is generally tubular, with a longitudinal axis A, and it comprises, disposed coaxially:

a radioprotective tubular sleeve 722, made of a radioprotective material providing protection against ionizing radiation (for example tungsten and/or lead glass), a support ring 723, disposed within the tubular sleeve 722, and adapted to support the vial adaptor 4, and a jacket 724, disposed outside of said tubular sleeve 722 adapted to maneuver the support ring 723.

The tubular sleeve 722, having a longitudinal axis C, is delimited by an inner face 7221, by an outer face 7222, an end 7223, said "lower end", and by an end 7224, said "upper end".

At its lower end 7223, the inner face 7221 of the tubular sleeve 722 includes said thread 721 adapted to cooperate with the thread 716 of the container body 71. These threads 721 and 716 allow detachably mounting of the vial adaptor support structure 72 onto the opening 711 of the container body 71.

At its upper end 7224, the outer surface 7222 of the tubular sleeve 722 includes a thread 7225 adapted to cooperate with the thread 91 of the cover 9.

In alternative embodiments, the threads 716, 721, 7225 and 91 of the container body 71, tubular sleeve 722 and cover 9, can be replaced by other means of removable attachment such as quarter turn or bayonet type assemblies.

The support ring 723 is delimited by an inner surface 7231, by an outer surface 7232, by an end 7233, said "lower end", oriented towards the lower end 7223 of the tubular sleeve 722, and by an end 7234, said "upper end", oriented towards the upper end 7224 of the tubular sleeve 722.

The inner surface 7231 of the support ring 723 defines an internal space 7231a whose geometry is configured to receive the vial adaptor 4, by engagement of the front portion 43 thereof through the lower end 7233, and so as to block translation of said vial adaptor 4, in this engagement direction along its longitudinal axis L1, and to prevent its rotation about said longitudinal axis L1.

For this, the inner surface 7231 comprises:

first positioning means 7235, in the form of a conical surface, adapted for the aforementioned blocking in translation, in cooperation with a complementary conical surface 44 of the vial adaptor 4, and second positioning means 7236, in the form of at least one lateral flat part (in this case two lateral flats 7236), against which planar side faces of the vial adaptor 4 are intended to be positioned for the aforementioned locking in rotation.

The support ring 723 may be made of plastic.

The jacket 724 is defined by an inner surface 7241, by an outer surface 7242, by an end 7243, said "lower end", oriented towards the lower end 7223 of the tubular sleeve 722 and the lower end 7233 of the support ring 723, and by an end 7244, said "upper end", oriented towards the upper end 7224 of the tubular sleeve 722 and the upper end 7234 of the support ring 723.

The inner surface 7241 of the jacket 724 is adapted to come opposite the outer face 7222 of the tubular sleeve 722.

At the upper end 7244 of the jacket 724, the outer surface 7242 includes a projecting bead 7245 to facilitate its handling, in view of its operation, as explained later in the description.

The jacket 724 can be made of plastic.

The vial adaptor support structure 72 comprises retention means configured for enabling releasable retention (i.e. releasable holding) of the vial adaptor 4, and transfer means for imparting to said vial adaptor 4 a (single) degree of freedom in longitudinal translation along its longitudinal axis L1, relative to said container 7 and in particular with respect to said attachment means 721. This enables the puncture of the closure member by a translation movement i.e. without rotation of the spike into the closure member.

For this purpose, the support ring 723 and the jacket 724 are joined together through fastening means constituted of two assembly lugs 726 and 727 which pass through oblong holes 728 formed in the tubular sleeve 722.

The two sets of lugs 726, 727 and oblong holes 728 are arranged diametrically opposite with respect to the longitudinal axis A.

The two oblong holes 728 comprise—a major axis (or length) extending parallel to the longitudinal axis A, and—a short axis (or width) slightly larger than the diameter of lugs 726, 727.

The first assembly lug 726 is shaped like a radial pin having an inner end 7261 provided with a thread 7262 which cooperates with a threaded hole 7237 formed in the support ring 723. The outer end 7263 of the radial pin 726 is housed in a cylindrical hole 7246 formed in the jacket 724.

This outer end 7263 comprises a groove-shaped recess 7264 enabling it to maneuver in rotation by a tool such as a screwdriver.

A shoulder 7265 formed on the radial pin 726, just before the thread 7262, constitutes a stop preventing said inner end 7261 from protruding out of the bulk of the support ring 723, into the inner space 7231a.

The second assembly lug 727 is shaped like a radial pin having an inner end 7271 provided with a thread 7272 which cooperates with a threaded hole 7238 formed in the support ring 723. The outer end 7273 of the radial pin 727 is housed in a cylindrical hole 7247 formed in the jacket 724.

This outer end 7273 includes a scroll wheel 7274 for its manual rotation maneuver.

A shoulder 7275 formed on the radial pin 727, just before the thread 7272, constitutes a stop which allows a slight protrusion of the inner end 7271 in the inner space 7231a of the support ring 723.

This slight protrusion is adapted so that the inner end 7271 of the radial pin 727 forms a bearing head having the opportunity to come to rest on the side of the vial adaptor 4 in place in the inner space 7231a, so as to tighten against the support ring 723 and constitute at least a part of the aforementioned retention means.

The radial pin 727 is indeed movable radially between:

an active position in which its inner end 7271 extends into said internal space 7231a of the support ring 723 (as shown in FIG. 11) and is adapted to abut against said vial adaptor 4, to assemble the latter with said support ring 723, and an inactive position wherein said inner end 7271 is adapted to be recessed, for example in the bulk of the thickness of the support ring 723, so as not to abut against said vial adaptor 4.

In an alternative embodiment, the radial pin 727 associated with the scroll wheel 7274 may be replaced by other means such as a button mounted on a support spring or the like.

Here, the radial pin 727 thus serves as fastening means between the support ring 723 and the jacket 724, and as retention means between, on one hand, the assembly comprising the support ring 723 and the jacket 724, and, on the other hand, the vial adaptor 4.

In an alternative embodiment these two functions may be provided separately, in which case the clamping pin will not be used in the connection between the support ring 723 and the jacket 724.

The length of the oblong holes 728 determines the maximum degree of freedom in translation between the tubular sleeve 722 and the assembly comprising the support ring 723 and the jacket 724 (this degree of freedom in translation being limited by the abutment of the assembly lugs 726, 727 against the ends of oblong holes 728).

As part of this maximum degree of freedom in translation, the vial adaptor support structure 72 includes indexing means, in at least one position, of the assembly comprising the vial adaptor 4, the support ring 723 and the jacket 724, relative the tubular sleeve 722.

In the present case, the vial adaptor support structure 72 includes indexing means with two positions, one high and the other low, consisting of:
- at least one lock of the retractable ball type 7227 (a ball associated with a spring), in this case three locks of the retractable ball type 7227, provided on a circular line of the outer surface 7222 of the tubular sleeve 722, which cooperates with
- two circular recesses 7248 and 7249 made on the inner face 7241 of the jacket 724.

It is understood that when the balls of the locks 7227 come in correspondence with the circular recess 7248, they are forced to enter in this recess and the assembly comprising the support ring 723, the jacket 724 and the vial adaptor 4 is indexed in the lower position relative to the tubular sleeve 722, that is to say, maintained in this low position by the pushing force applied by the springs on the balls (as shown in FIGS. 1 to 3, 6, 8, 10 and 12).

If an axial shifting force is applied by an operator on the assembly comprising the support ring 723, the jacket 724 and the vial adaptor 4, relative to the tubular sleeve 722, the balls of the locks 7227 can be matched with the circular recess 7249 for achieving high indexing position.

In said lowered position, the upper ends 7234 and 7244 of the support ring 723 and jacket 724 (extending at the same level or almost the same level), are located beneath the level of the upper portion 7224 of the tubular sleeve 722, the thread 7225 of said tubular sleeve 722 projecting over said jacket 724 and the front portion 43 of the vial adaptor 4 being completely or substantially completely surrounded by said tubular sleeve 722.

In said high position (FIG. 13) the upper ends of the support ring 723, the jacket 724 and the tubular sleeve 722 are located at substantially the same level, and the front portion 43 of the vial adaptor 4 protrudes, above the top of the tubular sleeve 722.

In an alternative embodiment the retractable ball lock 7227 may be replaced by other indexing means.

The vial 2 containing the radioactive solution S is placed in the container body 71 to protect operators against ionizing radiation emitted by said radioactive solution S.

To ensure optimum protection, the opening 711 of the container body 71 is closed by means of the cover 9, by screwing the thread 91 on the thread 716 of the cylindrical collar 715, as shown in FIGS. 4 and 5.

Preferably, the structure of the container body 71 and that of the associated cover 9, is adapted to retain the vial 2 in the container 7. More specifically, the vial 2 is clamped between the bottom 712 of the container body 71 and the cover 9.

Note that the container body 71 and the cover 9 are adapted to allow the reception and the retention of different vial models (for example "Mallinckrod", "IBA" or "GE-General Electric" models (registered trademarks)), optionally by means of a reported wedge 10 (i.e. a height adaptor) disposed between the bottom 712 of the container body 71 and the vial 2. In some embodiments, the height adaptor may be made of a compressible material so as to cushion the vial into the container body and provide some tolerance with regard to the vial dimensions. Such material may advantageously withstand alcoholic disinfection. For example, the height adaptor may be made of rubber, latex, foam, silicon or the like.

The cover 9 is also preferably equipped with an opening 92 associated with a hatch system 93 that allows, in the position of hatch 93 open, an injection or a removal of the solution S in the vial 2 by means of a syringe or using another suitable means, through the opening 92. In some embodiments, the hatch system may be operated without protruding out from the cover 9, for example by being configured to be pivoted in the opening plane to selectively cover and uncover the opening 92.

In the closed position of the hatch 93, the opening 92 of the cover 9 is closed by a material providing protection against ionizing radiation, and the vial 2 is then completely surrounded by a radioprotective material.

Operation of the Sampling and/or Injection Device 1

Starting from such a conditioning system, the sampling and/or injection of the radioactive solution S can be made by means of an equipment comprising a vial adaptor 4 and a syringe adaptor 5, as described below, with the vial adaptor support structure 72, as described below in connection with FIGS. 13, 14 and 15.

First, the vial adaptor 4 is placed in the vial adaptor support structure 72 by engaging its front portion 43 in the lower end 7233 of the support ring 723, after proper angular orientation, so that the flat portions 7236 come into correspondence of the aforementioned side flat surfaces of the vial adaptor 4, and this until the conical surface 44 of the vial adaptor 4 abuts (or is clamped) against the conical surface 7235 of the support ring 723.

The front portion 43 of the vial adaptor 4 is then located on the side of upper ends of the support ring 723, tubular sleeve 722 and jacket 724, of the vial adaptor support structure 72; and the hollow spike 42 of the vial adaptor 4 is located on the side of the lower ends of the support ring 723, tubular sleeve 722 and jacket 724 of the vial adaptor support structure 72.

The assembly comprising the support ring 723 and the jacket 724 is assembled with the vial adaptor 4 by tightening of the radial pin 727 by means of the scroll wheel 7274. In other words, the vial adaptor may secured in the vial adaptor support structure using the releasable retention means. The assembly support ring 723/jacket 724/vial adaptor 4 is then placed in the high position relative to the tubular sleeve 722 by positioning the ball locks 7227 in the lower recess 7249 of the jacket 724.

After removing the cover 9 of the container body 71, the vial adaptor support structure 72 is assembled with said container body 71 by screwing the thread 721 of the tubular sleeve 722 on the thread 716 of the neck of container 715. In other words, the vial adaptor support structure is then mounted on the body container using the detachable connection means.

There is provided a container 7 illustrated in FIG. 13, with the vial adaptor 4 positioned just above the vial 2, coaxially thereto, and in particular to its opening 711, and with the hollow spike 42 positioned facing the puncturable closure member 3 at a slight distance from the latter (e.g. of the order of a few millimeters).

In this position, the tubular sleeve 722 extends the protection of the container body 71 almost until the top of the vial adaptor 4.

The next operation consists in positioning the vial adaptor 4 on the upper portion of the vial 2, by lowering the assembly comprising the support ring 723, the jacket 724 and the vial adaptor 4, to ensure the piercing of the puncturable closure member 3, by the hollow spike 42 of the vial adaptor 4.

This piercing is designed optimally by the translation of the assembly comprising the support ring 723 and the jacket 724 on the tubular sleeve 722, guided by the assembly lugs 726, 727 that are movable in the oblong holes 728 (FIG. 14). In other words, a linear puncturing of the closure member is performed using the transfer means to translate the vial adaptor.

This translation is carried out until the ball locks 7227 enter the upper recess 7248 of the jacket 724. In other words, the indexing means may provide for a stopper configured to selectively maintain the vial adaptor in the high and low positions.

The cover 9 can then be positioned on the vial adaptor support structure 72 by engagement of its thread 91 with the upper thread 7225 of the tubular sleeve 722, as illustrated in FIGS. 15 and 16, to ensure a complete peripheral radioprotection, prior to further operations of sampling/injection of the radioactive solution S.

If necessary, after unscrewing the cover 9, the container 7 containing the vial 2 of radioactive solution S is then ready to receive the syringe 6 equipped with the syringe adaptor 5 (by assembling the front portions 43 and 52 of the vial adaptor 4 and syringe adaptor 5) as shown in FIGS. 1 to 3.

The assembly comprising the vial 2, the vial adaptor 4, the syringe adaptor 5 and the syringe 6 is then substantially completely covered with a radioprotective material providing protection against ionizing radiation. The syringe 6 can be used to carry out sampling and/or desired injection, and this syringe 6 can be separated from the vial 2 by disassembling the vial adaptor 4 with respect to the syringe adaptor 5 to perform other operations, such as a mixture of draw volume of radioactive solution S with a tracer before injection into a patient.

The vial adaptor 4 can be separated from the vial adaptor support structure 72 (in particular for its replacement) by unscrewing the tubular sleeve 722, and then by release of the radial pin 727 by means of the maneuver scroll wheel 7274.

Note that if the complementary conical surfaces 7235 and 45 of the support ring 723 and the vial adaptor 4 are made in such a way that they are sufficient to ensure the detachable connection between these two elements, then the clamping function of the radial pin 727, with the maneuver scroll wheel 7274, could be omitted.

The sampling and/or injection syringe 6, and its protection device 8 in the form of a radioprotective shield, are detailed in FIGS. 17 to 24.

The syringe 6, of conventional type, comprises a cylindrical body 61, having a longitudinal axis B, equipped at its front end 611 with an end tip 612 provided with an orifice for the passage of liquid to be sampled or to be injected, connected here to the rear portion 51 of the syringe adaptor 5.

At its rear end 613, the syringe body 61 has an opening 614 for the passage of a piston 62 with a maneuvering head 621.

The opening 614 of the syringe body 61 is bordered by lateral wings 615 for easy maneuvering of the piston 62.

The protection device 8 is in the form of a clamp comprising two half-jaws 81, 82 joined together by a hinge 83 associated with biasing means 84.

Each half-jaw 81, 82 includes a half-shell, respectively 811, 821, made of radioprotective material providing protection against ionizing radiation (for example tungsten), assembled with a plastic base 812, 822.

The two plastic bases 812, 822 each include a body 813, 823 provided with an inner face 814, 824, which inner faces 814, 824 are arranged opposite one another.

A longitudinal edge 815, 825 of each of the base body 813, 823 together form a portion of the hinge 83.

For this, each of said longitudinal edges 815, 825 comprises cylindrical elements 816, 826, intended to come into line with one another, for positioning a cylindrical axis 85 embodying the hinge 83.

The elastic return means 84 here comprise two spiral springs carried by the ends of the axis 85 and acting on the bases 812, 822 so as to tend to bring closer their inner faces 814, 824.

On the other hand, each of said bases 812, 822 includes an projection 817, 827 on the other side of the hinge 83 relative to the body 813, 823, which comprise operating arms for the opening and closing operations of the shaped clamp protection device 8.

The maneuvering means 83, 84, 817, 827 are adapted to provide the half-jaws 81, 82 with:
  a closed operative position (FIGS. 17 and 19 to 24), wherein they are constructed as cylinder, adapted to at least partially cover the syringe body 61, and
  an open inoperative position (FIG. 18), suitable for the introduction and extraction of the syringe 6, and in particular of the syringe body 61 with the syringe adaptor 5.

More specifically, the half-shells 811 and 821 each have a semi-cylindrical overall shape, whose concave portions are oriented opposite one another; and they are carried by the base body 813, 823 so as to allow:
  their juxtaposition to form a cylinder adapted to cover the entire length of the syringe body 61, and
  their separation by pivoting around the hinge 83, for the abovementioned operations of setting up and removal of the syringe 6.

In the embodiment illustrated in the figures, the half-shells 811, 821 comprise an protrusion 811a, 821a adapted to cover substantially entirely the syringe adaptor 5. In other words, said half-shells may include protrusions which projects longitudinally so as to at least partially cover the syringe adaptor.

These protrusions 811a, 821a for covering the syringe adaptor 5 includes a notch 86 allowing the passage of the aforementioned lateral extensions 521. This removes the requirement to have a complex form of protective half-shell, while the risk of release of radiation at this level is limited.

Figures 23, 24:
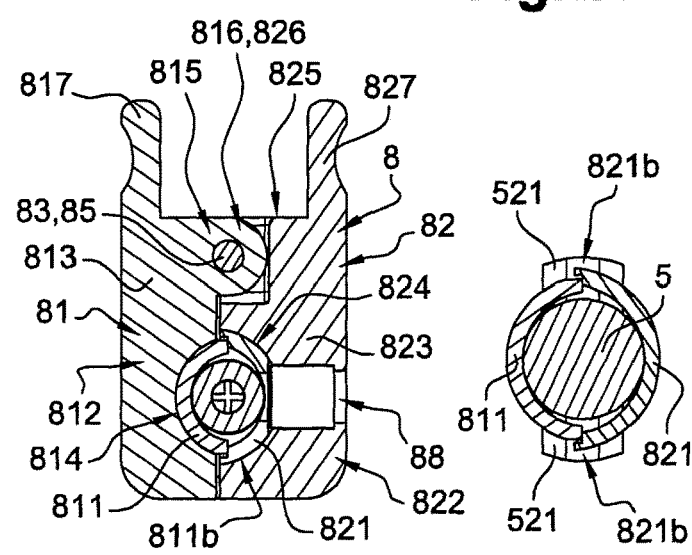
FIG. 23 is a sectional view taken along section lines 23-23 of FIG. 20.
FIG. 24 is a sectional view taken along section lines 24-24 of FIG. 20.

As can be seen in FIGS. 23 and 24, the two longitudinal sides of one of the half shells (in this case the half-shell 821) include a small projecting lip 821b adapted to overlie the longitudinal side which is in contact with the other half-shell (in this case the half-shell 811), in said closed position, so as to optimize protection.

The half-jaw bases 812, 822 comprising the base body 813, 823, the cylindrical portions 816, 826 and the projections 817, 827 are formed integrally by plastic injection molding.

Here, the base body 813, 823 cover the entire portion of the half shells 811, 821 to protect the syringe body 61; and the protrusions 811a, 821a intended to cover the syringe adaptor 5 are protruding and have no plastic base.

In alternative embodiments, the base body 813, 823 may cover the half shells 811, 821, 811a and 821a over a larger or shorter length.

Each half-shell 811, 821 is assembled with its base 812, 822 by means of screws 87 (here there are two per half shell).

On the other hand, to allow visual access to the contents of the syringe body 61, one of the half-jaws 81, 82, or both, may comprise a transparent window 88 extending through the half-shell 811, 821 and the associated base 812, 822, made of a material providing protection against ionizing radiation, such as lead glass.

It is well understood that such a protection device 8 in the form of hinged clamp is very easy to position on a syringe 6, by simple manual opening of the half-jaws 81, 82 (pivoting around the hinge 83 by pressing the arm 817, 827), then by introducing the entire syringe body 61/syringe adaptor 5, and then relaxing the bearing force on the arms 817, 827.

An abutment of one end of the half shells 811, 821 against the lateral wings 615 of the syringe body 61 facilitates this positioning.

The syringe 6 can be removed from its protection device 8 in a similar way.

Such a protection device 8, designed as a clamp, can be adapted to other types of syringes, for example syringes that are devoid of a syringe adaptor; and it can be considered independently of the container 7 as described above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

The invention claimed is:

1. A device useful for sampling and/or injection of a radioactive solution in a vial, wherein the vial has an opening closed by a puncturable closure member, the device comprising:
    a container adapted to receive said vial and a vial adaptor, said vial adaptor having a longitudinal axis, provided at a first end with a hollow spike adapted to pierce said puncturable closure member when the vial adaptor is mounted on the vial and at a second end with connection means adapted for its removable connection to a syringe adaptor,
    the container comprising:
        a container body adapted to receive said vial, the container body having an opening, and
        a vial adaptor support structure configured for being mounted onto the opening of the container body, and comprising retention means configured for enabling releasable retention of said vial adaptor within said vial adaptor support structure,
    wherein the vial adaptor support structure and the container body are made at least partially of a radioprotective material for providing protection against ionizing radiation;
    wherein the vial adaptor support structure further comprises transfer means for imparting to said vial adaptor a degree of freedom in longitudinal translation along its longitudinal axis;
    wherein the vial adaptor support structure is generally tubular with a longitudinal axis and comprises:
        a tubular sleeve having a first end provided with attachment means configured for enabling mounting of the vial adaptor support structure onto the opening of the container body,
        a support ring, received in said tubular sleeve, coaxial with the tubular sleeve, and defining an internal space for the reception of said vial adaptor,
    wherein the transfer means are further configured for imparting to said support ring a degree of freedom in longitudinal translation along said longitudinal axis with respect to said tubular sleeve, and
    the retention means are further configured for enabling connection of said vial adaptor with said support ring.

2. The device according to claim 1, characterized in that the vial adaptor support structure comprises a jacket for operating said support ring according to said degree of freedom in translation, said jacket at least partially surrounding said tubular sleeve and including fastening means configured to fasten said jacket with said support ring.

3. The device according to claim 2, characterized in that said fastening means are in the form of at least two assembly lugs connecting said jacket and said support ring and which pass through oblong holes in said tubular sleeve.

4. The device according to claim 3, characterized in that said retention means comprise a radial bearing pin secured with said jacket and/or said support ring, wherein said bearing pin has an outer end accessible on an outer periphery of said jacket, provided with an operating member, and an inner end forming a bearing head, and wherein said bearing pin is movable radially between:
    an active position in which said bearing head extends into said internal space of said support ring and is adapted to abut against said vial adaptor in order to assemble said vial adaptor with said support ring and/or said jacket, and
    an inactive position in which said bearing head does not abut against said vial adaptor.

5. The device according to claim 4, characterized in that said bearing pin is also one of said assembly lugs.

6. The device according to claim 1, characterized in that the device further includes indexing means to at least one position, of the assembly comprising the vial adaptor, the support ring and the jacket, relative to said tubular sleeve.

7. The device according to claim 6, characterized in that said indexing means comprise at least one retractable ball lock mounted on one of the tubular sleeve or the jacket cooperating with a recess provided on the other of the tubular sleeve or the jacket.

8. The device according to claim 1, characterized in that said support ring comprises first positioning means configured for blocking said vial adaptor in a direction along its longitudinal axis, and second positioning means adapted to prevent rotation of said vial adaptor about said longitudinal axis.

9. The device according to claim 1, further comprising:
a syringe comprising a syringe body, a piston and a syringe adaptor configured for connection to said vial adaptor, and
a protection device shaped as a shield made of radioprotective material providing protection against ionizing radiation, wherein said protection device covers at least partially said syringe body and said syringe adaptor.

* * * * *